US00PP36546P2

(12) United States Plant Patent
Boyer

(10) Patent No.: US PP36,546 P2
(45) Date of Patent: Mar. 11, 2025

(54) ***AGASTACHE* PLANT NAMED 'Sierra Purple'**

(50) Latin Name: ***Agastache* hybrid**
Varietal Denomination: Sierra Purple

(71) Applicant: Nathan Randall Boyer, Prescott, AZ (US)

(72) Inventor: Nathan Randall Boyer, Prescott, AZ (US)

( * ) Notice: Subject to any disclaimer, the term of this patent is extended or adjusted under 35 U.S.C. 154(b) by 11 days.

(21) Appl. No.: 18/445,649

(22) Filed: Dec. 13, 2023

(51) Int. Cl.
*A01H 5/02* (2018.01)
*A01H 6/50* (2018.01)

(52) U.S. Cl.
USPC ..... Plt./399

(58) Field of Classification Search
USPC ..... Plt./399
See application file for complete search history.

*Primary Examiner* — Susan McCormick Ewoldt
(74) *Attorney, Agent, or Firm* — J. Adele Plotkin

(57) ABSTRACT

A new and distinct cultivar of hyssop useful in landscaping, *Agastache* plant named "Sierra Purple" is disclosed characterized by corollas that emerge red and become purple/pink as corolla matures; blooming from Mid/Late spring until frost; a larger habit in both height and width; vigorous branching and inflorescence quantity; purple stems and foliage year round becoming deep purple when stressed; excellent vigor; and good winter hardiness.

6 Drawing Sheets

Figure 1:
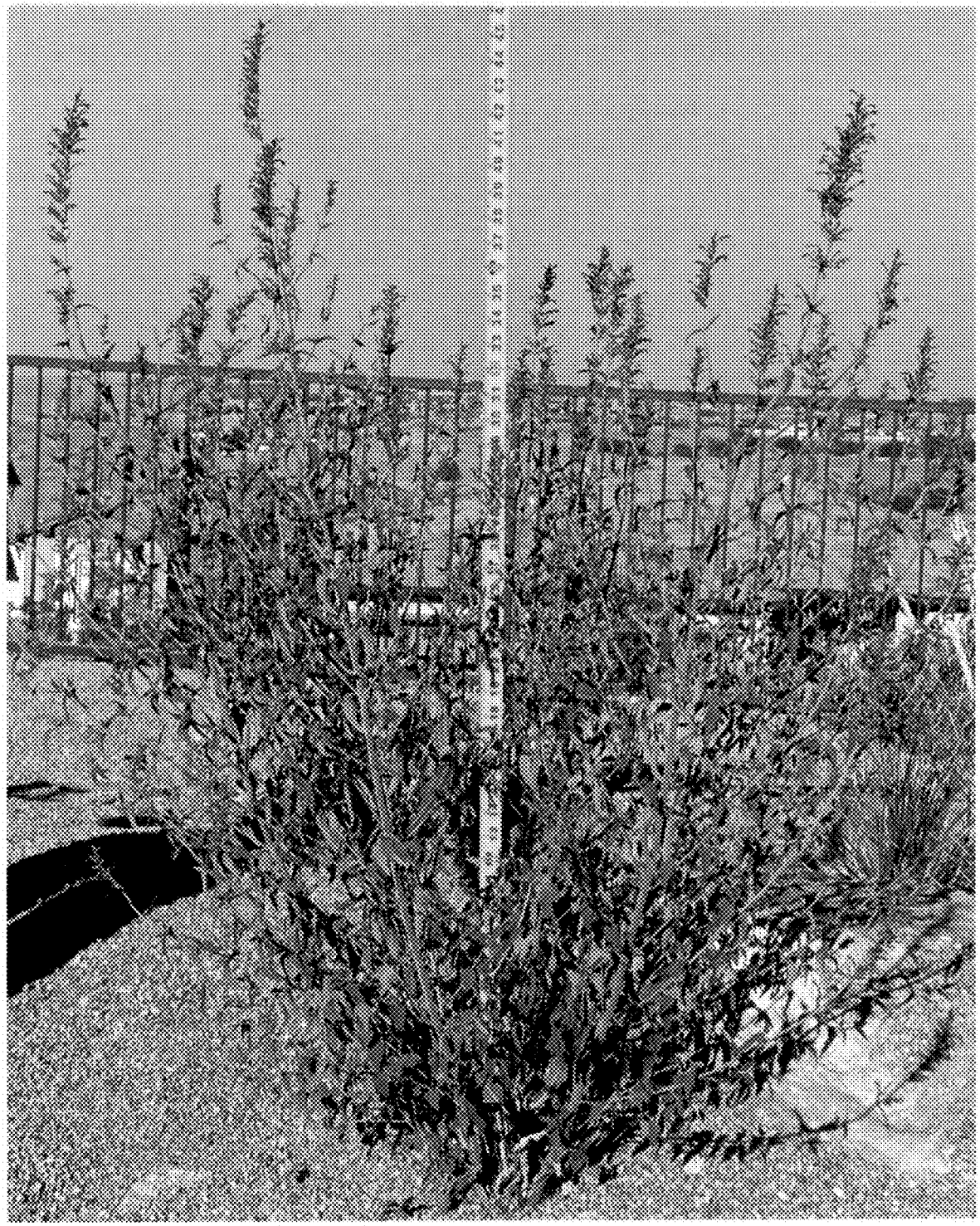

Latin name of genus and species: *Agastache* hybrid.
Variety designation: 'Sierra Purple'.

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A SEQUENCE LISTING, A TABLE, OR A COMPUTER PROGRAM LISTING COMPACT DISC APPENDIX

Not applicable

BACKGROUND OF THE INVENTION

A distinct cultivar of *Agastache* hybrid given the name, 'Sierra Purple' is herein described. The parents of this new hybrid cultivar include are the species *Agastache cana* 'Bolero' and *Agastache rupestris* 'Glowing Embers'. It is not known which of the parents was male and which was female. This new cultivar came out of unplanned hybridization in a backyard garden located in St. Francis, Kansas, which is in NW Kansas, USDA hardiness zone 5b. At that time, this new cultivar was selected for its upright habit, stem and foliage color, hardiness, extended bloom time, and number of inflorescences.

Compared to 'Bolero' (unpatented plant) this new cultivar is much larger (height and width), with increased foliage fragrance, leaves that appear narrower, extended bloom time, and enlarged inflorescences. This new cultivar is at least one to two feet taller than 'Bolero' and at least 1-2 feet wider. The leaves appear narrower since the leaf length is two to three times longer than 'Bolero' while the leaf width is about the same. Further, 'Bolero' has pink and magenta flower colors whereas this new cultivar has purple flowers as detailed below. The inflourescences are proportionately larger in this new cultivar than in 'Bolero' given the larger overall plant size.

Compared to 'Glowing Embers' (unpatented plant) this new cultivar has different characteristics including being is-larger, possessing purple stems and purple/green foliage, and having a more upright habit, purple/pink corollas, and broader leaves. This new cultivar is at least a foot taller than and twice the width of the parent 'Glowing Embers'. The cultivar leaves are proportionately larger and hence seem broader than 'Glowing Embers'. Unlike the new cultivar, 'Glowing Embers' has gray-green foliage and orange to orange-red flowers.

Applicant is not aware of any other cultivar that has a similar level of persistent purple coloring as seen in 'Sierra Purple'. However there are multiple species known as Purple Giant Hyssop such as "*Agastache scrophulariifolia*" and *Agastache rugosa*. The former is an endangered species wildflower that can grow taller than 'Sierra Purple' by one to two feet. It has white to lavender flower spikes, leaves of two by four inches size that are more than twice the size of those of 'Sierra Purple', and stalks of medium-green color, strong, and erect. In the second comparison, the 'Sierra Purple' cultivar is at least a foot taller and a foot wider than *Agastache rugosa*, The 'Golden Jubilee' cultivar of "*Agastache rugosa*" has golden colored leaves and lavender-blue flower spikes. In general. *Agastache rugosa* derivatives tend to have violet-pink flowers and are not very winter hardy.

The new variety has been reproduced only by asexual reproduction (stem tip cuttings) in well draining soil of a garden in Prescott, Arizona. Each of the progeny exhibit identical characteristics of original plant.

The present invention has not been evaluated under all possible environmental conditions.

SUMMARY OF THE INVENTION

This hybrid cultivar of an *Agastache* plant exhibits the following characteristics that make it unique when grown under standard horticultural practice:

1. Purple stems and foliage year round becoming a deeper purple when stressed.
2. A larger habit in both height and width
3. Corollas that emerge purplish red and become purple/pink as the corolla matures
4. Blooms from Mid/Late spring until frost
5. Vigorous branching and inflorescence quantity
6. Excellent vigor
7. Good winter hardiness

BRIEF DESCRIPTION OF THE PHOTOGRAPHS

FIG. 1 Subject *Agastache* cultivar of over 45 inches tall as per measuring tape displayed.

Figure 2:
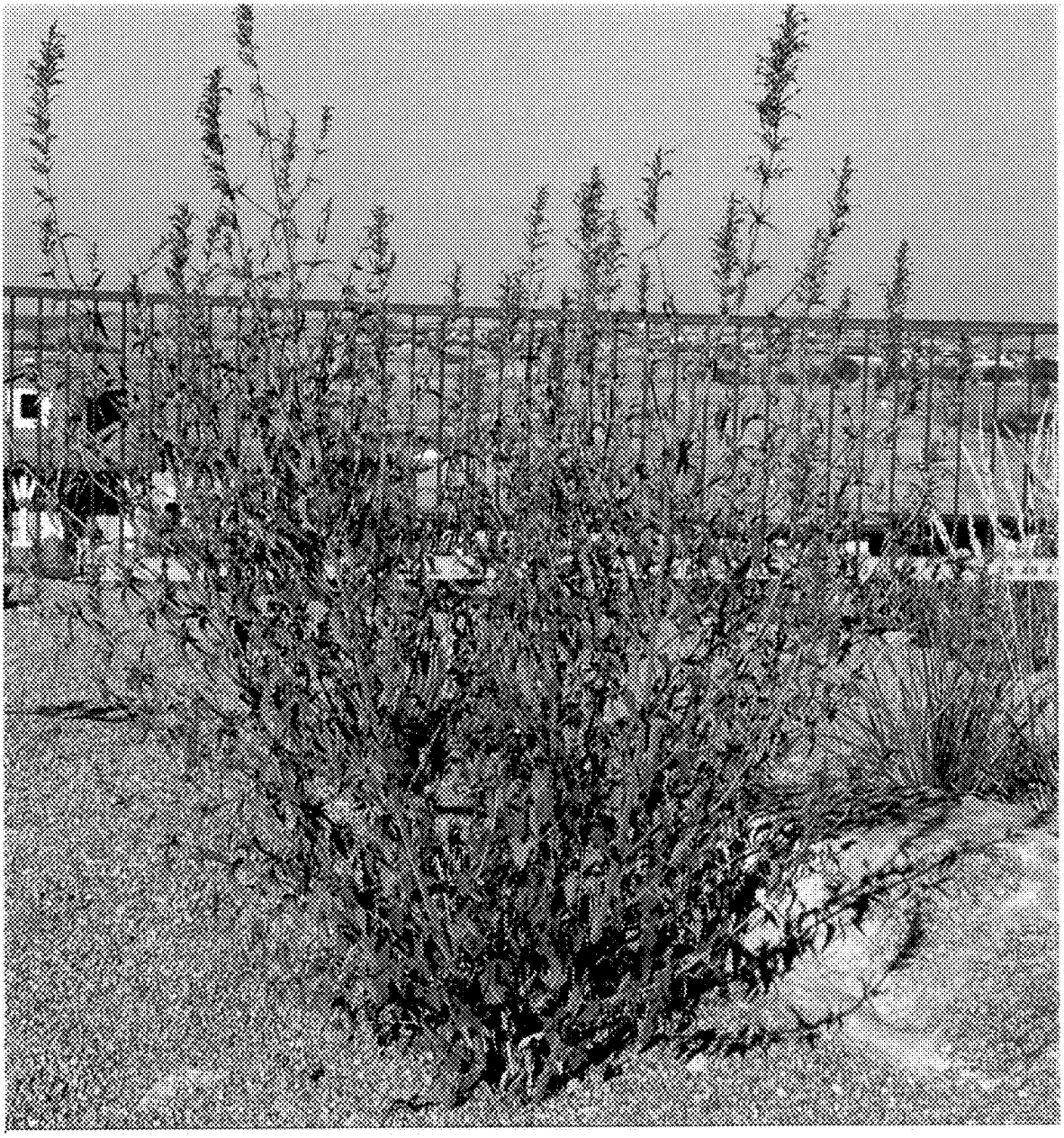

FIG. 2 Subject *Agastache* cultivar of over 40 inches width as per measuring tape displayed.

Figure 3:
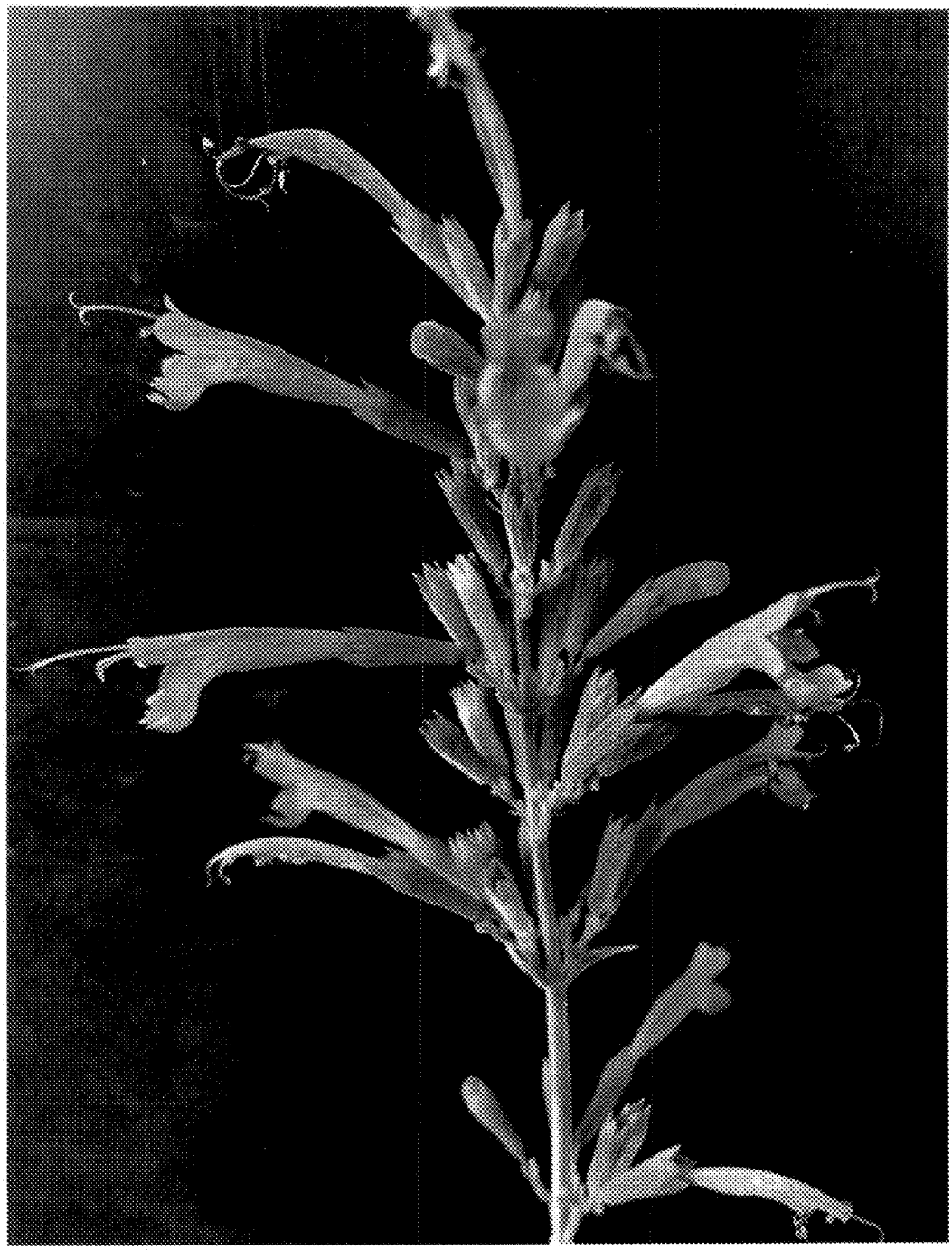

FIG. 3 Example 1 of subject *Agastache* cultivar flowers.

Figure 4:
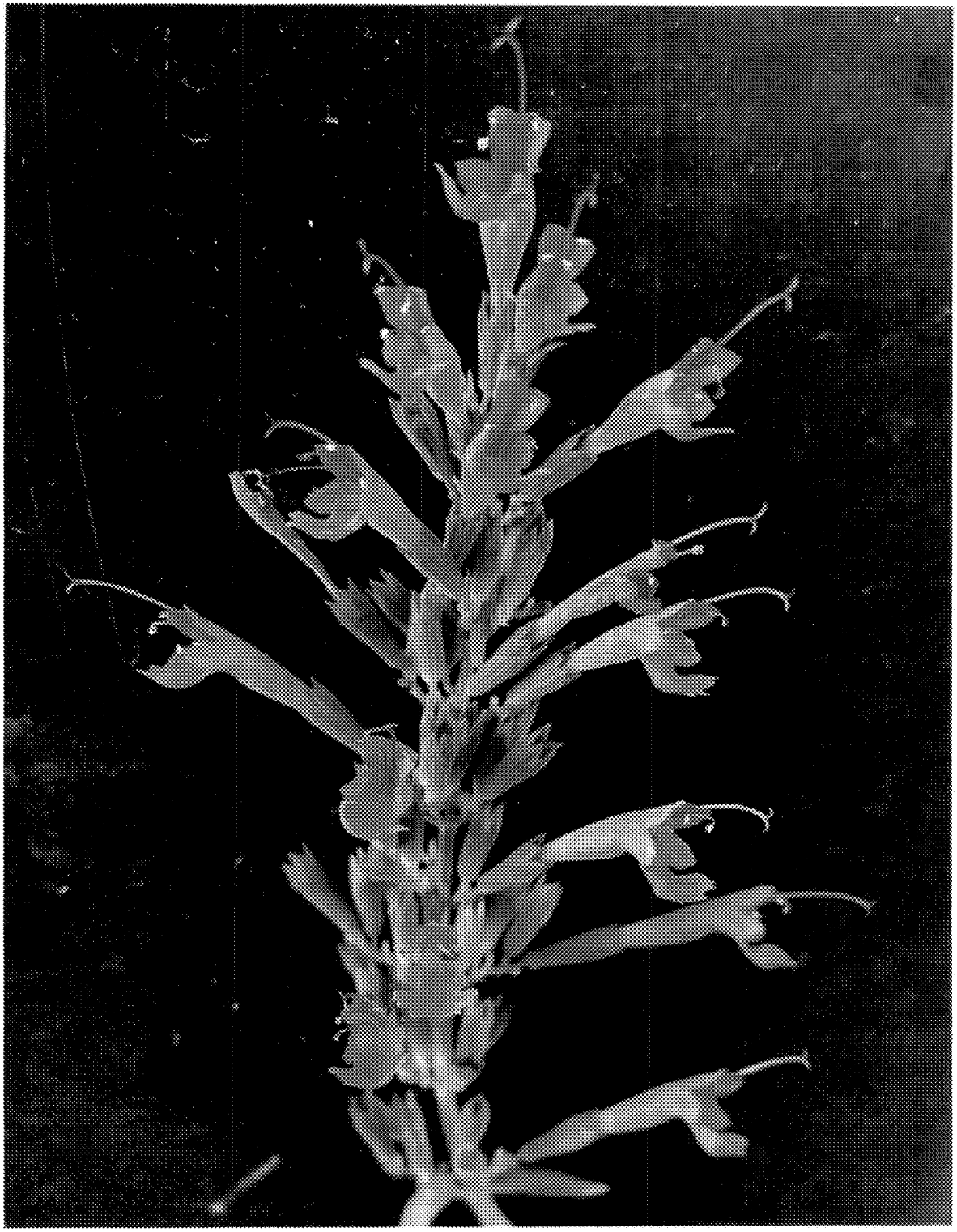

FIG. 4 Example 2 of subject *Agastache* cultivar flowers.

Figure 5:
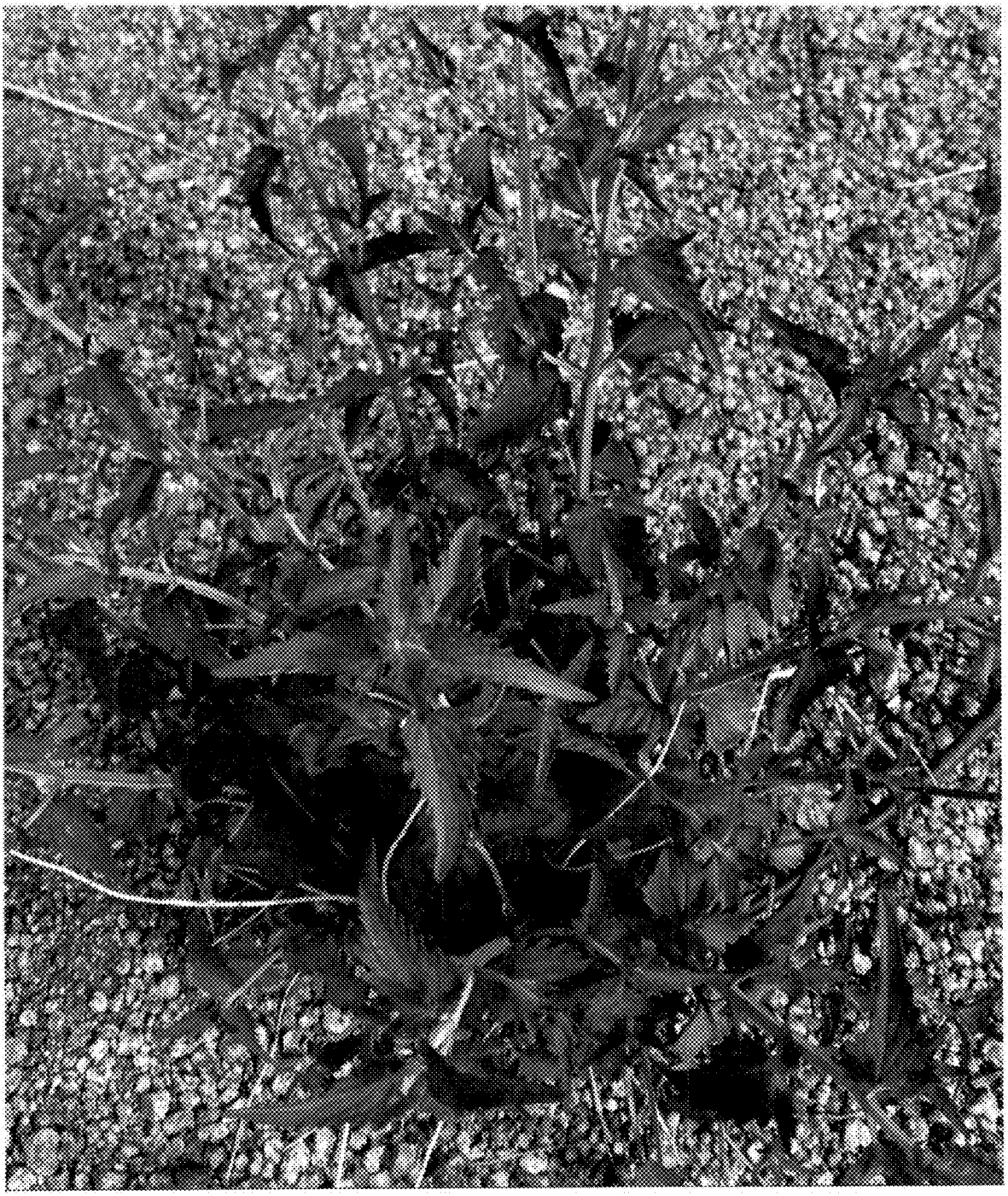

FIG. 5 Subject *Agastache* cultivar displaying dark purple colored leaves.

Figure 6:
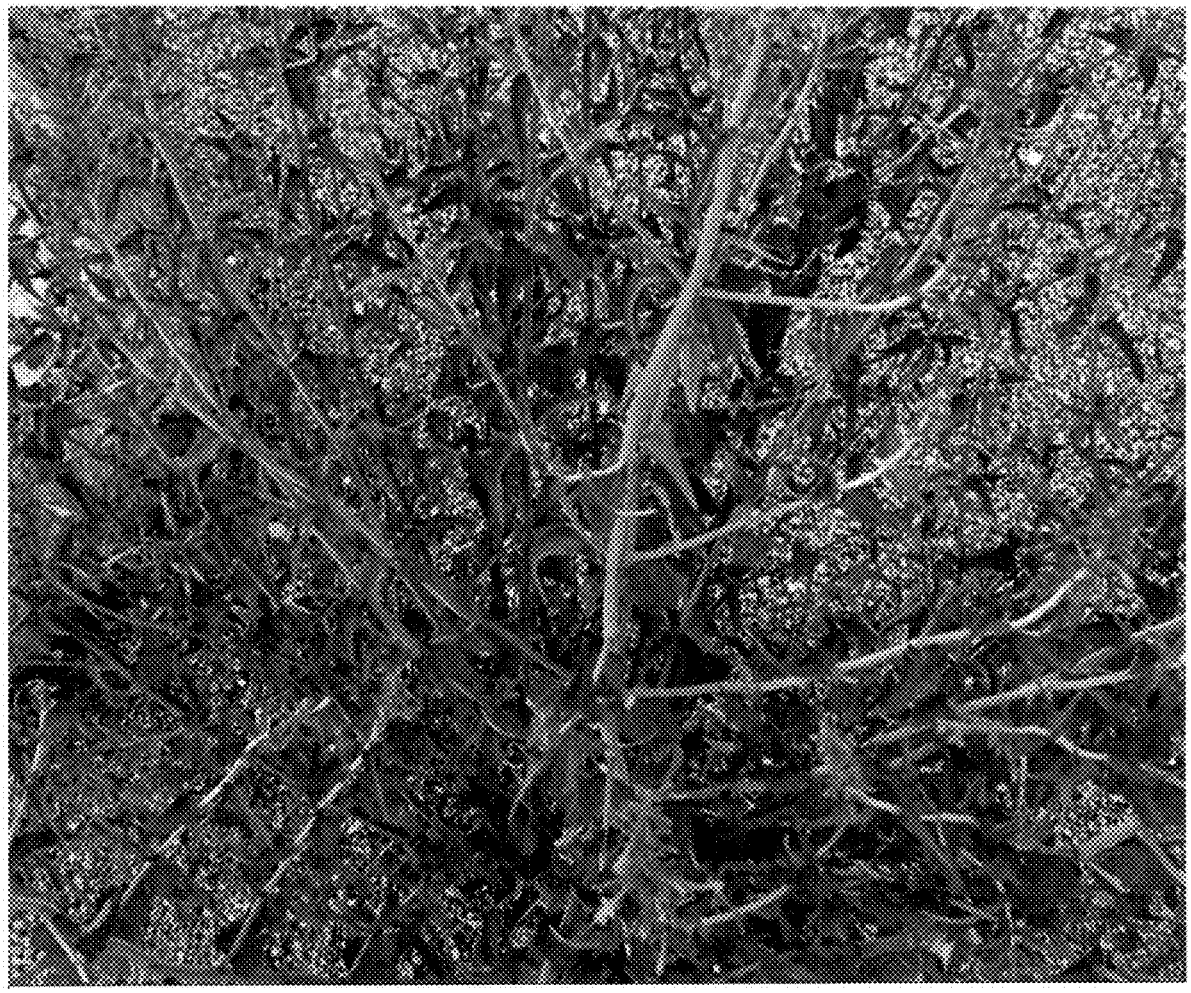

FIG. 6 Subject *Agastache* cultivar, flowering with dense dark foliage.

DETAILED PLANT DESCRIPTION

The following is detailed description of the new *Agastache* cultivar [KS plant] based on observation of a 3 year old established plant at the end of June, 2020 growing in full sun in a garden of well draining soil in Prescott AZ, USDA hardiness zone 7. Temperatures range from a high of 105° F. to lows between 5-10° F. Average yearly precipitation is ~16". Discovered in garden located in Saint Francis, KS, this plant has seen temperatures as low as −14° F. KS plant was then transplanted to a garden in Prescott, AZ. The color descriptions are all based on The Royal Horticultural Society Colour Chart, $6^{th}$ edition, 2019 reprint.

Plant:

*Form*.—Upright, bushy.

*Type*.—Herbaceous perennial.

*Cold hardiness*.—USDA Zone 5-9.

Size: Can grow up to 104 cm wide and 117 cm tall.

Vigor: Excellent.

Branching: 15 main stems from the base, these branch at every node. Branches average two mm in diameter and are the same color as the stems.

Stem: Square in cross section, pubescent, internodes range on average 6-7 to cm long, Greyish Yellow Green 191B to Yellow Green 143 D with Moderate Reddish Purple N79D hues.

*Roots*.—Moderate Yellow 160 A (from plants in soil and not from cuttings at transplant), fibrous, and plants root easily from stem tip cuttings.

Leaf:

*Type*.—Simple.

*Arrangement*.—Opposite.

*Shape*.—Deltoid-ovate.

*Venation*.—Pinnately reticulate.

*Margins*.—Crenate-serrate.

*Apex*.—Acute.

*Base*.—Rounded with mild oblique.

*Blade size*.—On average is 35 mm (31-45 mm) long and 16 mm (15-18 mm) wide.

*Surface texture*.—Pubescent on both sides.

*Petiole description*.—4 mm long by 1 mm wide, pubescent, Greyish Yellow Green 191B to Yellow Green 143 D with Moderate Reddish Purple N79D hues.

*Leaf color*.—Top side is Greyish Yellow Green 191A, vein is Reddish Purple close to Strong Reddish Purple NN78C or to Moderate Reddish Purple N79D or to Light Reddish Purple NN74C; bottom side is Greyish Yellow Green 191A tinted Reddish Purple close to Strong Reddish Purple NN78C or to Moderate Reddish Purple N79D or to Light Reddish Purple NN74C, vein is Reddish Purple close to Strong Reddish Purple NN78C or to Moderate Reddish Purple N79D or to Light Reddish Purple NN74C. When stressed the foliage on top and bottom appears to become a more intense purple closer to a darker purple within the range noted. The apparent visible intensity is variable according to the level of stress and the type of ambient light. All colors may appear different under different lighting conditions.

*Fragrance*.—Aromatic.

Inflorescence:

*Type*.—Spike composed of up to 20 whorl-like paired panicles of racemes.

*Number of flowers*.—Up to 2,000 to 3,000 per spike.

*Size of inflorescence*.—Grows up to 26 cm tall and 3.5 cm wide.

*Peduncle*.—Grows up to 6.5 cm long and up to 2 mm wide, pubescent, Greyish Yellow Green 191B to Yellow Green 143 D with Moderate Reddish Purple N79D hues.

*Pedicel*.—Grows up to 7 mm long, pubescent, Light Reddish Purple NN74C.

*Bloom period*.—Late May through frost in Prescott, AZ.

Flower bud:

*Size*.—15 mm long and 2 mm wide.

*Description*.—Tubular.

*Surface texture*.—Pubescent.

*Color*.—Strong Purplish Red 54A to 54B.

Flower:

*Type*.—Zygomorphic.

*Shape*.—Bilabiate, tubular.

*Size*.—21 mm long and 3-4 mm wide.

*Corolla description*.—Corolla emerges a Purplish Red 58C and grows to 20 mm long and spreads to 4 mm wide; both sides vary between Strong Reddish Purple NN74B-C and Deep Purplish Pink N66D; glabrous inside and pubescent outside, tube 15 mm long and 1-3 mm wide; two upper lobes joined 3 mm long and 2 mm wide, each having subacute tips with entire margins; three lower lobes, center lobe 4 mm wide by 3 mm long with a obcordate tip with serrate margins and side lobes 2 mm long by 2 mm wide with subacute tips with entire margins.

*Calyx description*.—Campanulate, 5-8 mm long and 1-2 mm wide, pubescent outside and glabrous inside, 5 lobed, lobes 2 mm long, entire, acuminate, Strong Reddish Purple NN74B to Light Reddish Purple NN74C.

*Pistil description.*—21 mm long and 0.5 mm wide, style white NN155D blending to Light Reddish Purple NN78D at two parted stigma, 1 mm deep.

*Stamen description.*—Four in number, paired and exerted, top two 29 mm long and bottom two 25 mm long, filaments Light Reddish Purple NN78D, anthers 1 mm long, Light Reddish Purple NN78D.

*Fragrance.*—Aromatic.

*Lastingness.*—A spike blooms for 20 weeks on the plant.

Fruit/seed: 1 nutlet, 1 to 1.5 mm long, ovoid, Dark Greyish Yellowish Brown N199B to Moderate Yellowish Brown N199C, low fertility.

Pests and diseases: The new cultivar is typical to the genus. No resistances to pests or diseases are known to date. No problems have been found in Prescott, AZ or Saint Francis, KS.

That which is claimed (currently amended) is:

1. A new and distinct cultivar of *Agastache* plant named 'Sierra Purple' as herein described and illustrated.

* * * * *